United States Patent
Geng (10) Patent No.: US 7,107,116 B2
(45) Date of Patent: Sep. 12, 2006

(54) DIFFUSE OPTICAL TOMOGRAPHY SYSTEM AND METHOD OF USE

(75) Inventor: Z. Jason Geng, Rockville, MD (US)

(73) Assignee: Genex Technologies, Inc., Kensington, MD (US)

( * ) Notice: Subject to any disclaimer, the term of this patent is extended or adjusted under 35 U.S.C. 154(b) by 311 days.

(21) Appl. No.: 10/654,225

(22) Filed: Sep. 2, 2003

(65) Prior Publication Data

US 2004/0087862 A1    May 6, 2004

Related U.S. Application Data

(60) Provisional application No. 60/407,304, filed on Sep. 3, 2002.

(51) Int. Cl.
*G08F 19/00* (2006.01)

(52) U.S. Cl. .................. 700/117; 356/432; 600/309

(58) Field of Classification Search ............... 700/110, 700/117, 166; 356/302, 305, 432; 600/309–312, 600/321, 322, 328, 329, 473–478
See application file for complete search history.

(56) References Cited

U.S. PATENT DOCUMENTS

| | | | | |
|---|---|---|---|---|
| 5,675,407 | A | * | 10/1997 | Geng ........................ 356/147 |
| 5,835,617 | A | * | 11/1998 | Ohta et al. .................. 382/131 |
| 5,865,754 | A | * | 2/1999 | Sevick-Muraca et al. ... 600/476 |
| 6,075,610 | A | * | 6/2000 | Ueda et al. .................. 356/432 |
| 6,083,486 | A | * | 7/2000 | Weissleder et al. .......... 424/9.6 |
| 6,239,868 | B1 | * | 5/2001 | Jung et al. .................... 356/73 |
| 6,615,063 | B1 | * | 9/2003 | Ntziachristos et al. ...... 600/312 |
| 2002/0072677 | A1 | * | 6/2002 | Sevick-Muraca et al. ... 600/473 |

\* cited by examiner

*Primary Examiner*—Leo Picard
*Assistant Examiner*—Chad Rapp
(74) *Attorney, Agent, or Firm*—Steven L. Nichols; Rader, Fishman & Grauer PLLC (57) ABSTRACT

An improved diffuse optical tomography system for in vivo non-contact imaging includes an illumination source for illuminating a specimen, a spectrum source for projecting a spectrum onto the specimen, at least one sensor configured to capture the response of the specimen to the illumination and to the projection of said spectrum.

12 Claims, 6 Drawing Sheets

DIFFUSE OPTICAL TOMOGRAPHY SYSTEM AND METHOD OF USE

RELATED APPLICATIONS

The present application claims priority under 35 U.S.C. §119(e) from the following previously-filed Provisional Patent Applications, U.S. application Ser. No. 60/407,304, filed Sep. 3, 2002 by Geng, entitled "Enhance the Accuracy of Diffuse Optical Tomography Using 3D Camera" which is incorporated herein by reference in its entirety.

The present application is related to U.S. application Ser. No. 09/616,723 by Geng entitled "Three-Dimensional Dental Imaging Method and Apparatus Having a Reflective Member." application Ser. No. 09/616,723 is a Continuation-in-Part of U.S. application Ser. No. 09/616,723 by Geng entitled, "Three-Dimensional Dental Imaging Method and Apparatus." application Ser. No. 09/616,723 claims priority from U.S. Provisional Application. No. 60/144,010, filed Jul. 15, 1999. All three of these previous applications are hereby incorporated by reference in their entireties.

The present application is also related to (1) U.S. Provisional Patent Application No. 60/375,934, "Method and Apparatus for Generating Structural Pattern Illumination" filed Apr. 26, 2002; (2) U.S. Provisional Patent Application No. 60/178,695, "Improvement on the 3D Imaging Methods & Apparatus" filed Jan. 28, 2000; (3) U.S. Patent application Ser. No. 09/770,124, "3D Surface Profile Imaging Method & Apparatus Using Single Spectral Light Condition" filed Jan. 26, 2001; (4) PCT Patent Application No. PCT/US01/18644, "3D Surface Profile Imaging Method & Apparatus Using Single Spectral Light Condition" filed Jun. 11, 2001; and (5) U.S. patent application Ser. No. 09/771,531, "Method & Apparatus for 3D Imaging Using Light Pattern Having Multiple Sub-Patterns" filed Jan. 29, 2001. All of these previous applications are hereby incorporated by reference in their entireties.

BACKGROUND

Diffuse Optical Tomography (DOT) is a functional imaging modality that reveals physiological parameters, such as oxygen saturation of hemoglobin and blood flow, based on intrinsic tissue contrast, molecular tissue function, and gene-expression based on extrinsically administered fluorescent probes and beams. DOT offers several potential advantages over existing radiological techniques, such as non-invasive and non-ionizing imaging.

DOT imaging includes illuminating the tissue with a light source and measuring the light leaving the tissue with a sensor. A model of light propagation in the tissue is developed and parameterized in terms of the unknown scattering and/or absorption as a function of position in the tissue. Then, using the model together with the ensemble of images over all the sources, one attempts to invert the propagation model to recover the scatter and absorption parameters.

A DOT image is actually a quantified map of optical properties and can be used for quantitative three-dimensional imaging of intrinsic and extrinsic adsorption and scattering, as well as fluorophore lifetime and concentration in diffuse media such as tissue. These fundamental quantities can then be used to derive tissue oxy- and deoxy-hemoglobin concentrations, blood oxygen saturation, contract agent uptake, and organelle concentration. Such contrast mechanisms are important for practical applications such as the measurement of tissue metabolic activity, angiogenesis and permeability for cancer detection as well as characterizing molecular function.

A typical DOT system uses lasers so that specific chromophores are targeted and the forward model is calculated for the specific wavelengths used. Laser diodes have been customarily used as light sources since they produce adequate power and are stable and economical. Light is usually directed to and from tissue using fiber guides since this allows flexibility in the geometrical set-up used. For optical coupling, the fibers must be in contact with tissue or a matching fluid. Use of the matching fluids helps to eliminate reflections due to mismatches between indices of refraction between silica, air, and tissue.

Advanced DOT algorithms require good knowledge of the boundary geometry of the diffuse medium imaged in order to provide accurate forward models of light propagation within this medium. A forward model is a representation of the representative characteristics of the volume being studied. Currently, these boundary geometries are forced into simple, well known shapes such as cylinders, circles, or slabs. In addition to not accurately representing the shape of the specimen to be analyzed, the use of these shape forces the specimen to be analyzed to be physically coupled to the shape either directly or by the use of a matching fluid as discussed above.

SUMMARY

An improved diffuse optical tomography system for in vivo non-contact imaging includes an illumination source for illuminating a specimen, a spectrum source for projecting a spectrum onto the specimen, at least one sensor configured to capture the response of the specimen to the illumination and to the projection of said spectrum.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

Throughout the drawings, identical reference numbers designate similar, but not necessarily identical, elements.

DETAILED DESCRIPTION

An improved diffuse optical tomography system for in vivo non-contact imaging includes an illumination source for illuminating a specimen, a spectrum source for projecting a spectrum onto the specimen, at least one sensor configured to capture the response of the specimen to the illumination and to the projection of the spectrum. The improved diffuse optical tomography system rapidly captures three-dimensional boundary geometry of and the corresponding diffuse optical tomography measurements of a specimen.

As used herein, 'pixel' shall be broadly understood to mean any picture element. As used herein, specimen shall be broadly understood to mean any volume or surface to be analyzed.

In the following description, for purposes of explanation, numerous specific details are set forth in order to provide a thorough understanding of the present method and apparatus. It will be apparent, however, to one skilled in the art that the present method and apparatus may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

EXEMPLARY STRUCTURE

Figure 1:
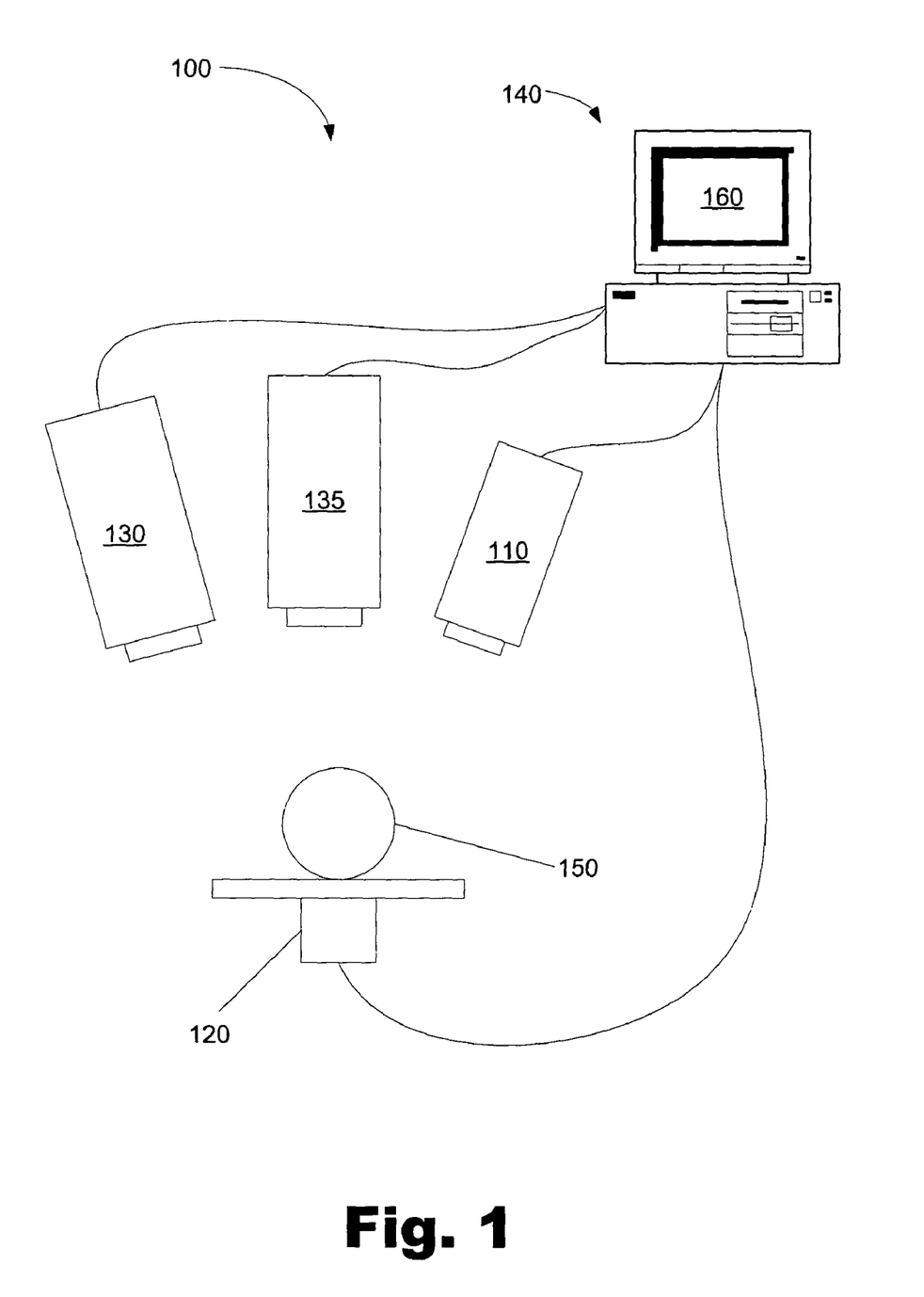
FIG. 1 illustrates a schematic view of an improved diffuse optical tomography system according to one exemplary embodiment.

FIG. 1 illustrates an improved DOT system (100) that generally includes a spectrum source assembly (110), an illumination assembly (120), and a 3D sensor assembly (130) and DOT sensor assembly (135) coupled to a processing device such as computer (140). The spectrum source assembly (110) projects light onto and the illumination assembly (120) projects light onto and through a specimen (150). The sensor assemblies (130, 135) capture the reaction of the specimen (150) in response to the applied light, and convey that information to the computer (140). The computer processes the information and displays the results on a monitor (160). Any 3D camera sensor and DOT sensor assembly may be used.

One example of a suitable 3D sensor is one that is configured to be used with a spectrum source assembly (110). The spectrum source assembly (110) is configured to project a spectrum of light of spatially varying wavelengths in the visible range onto the specimen (150). The response of the specimen to the applied light may be used to determine three-dimensional boundary conditions of the specimen. The three-dimensional boundary is determined by utilizing triangulation. A triangle is uniquely formed by the distance between the spectrum source assembly (110), the sensor assembly (130), and the point on the specimen (150). The spectrum source assembly (110) may include a linear variable wavelength filter (LVWF, not shown). Light projected from the spectrum source assembly through the LVWF falls onto the specimen (150) as a rainbow spectrum. The wavelength of the coated color of the LVWF in a specific location is linearly proportional to the displacement of the location from the LVWF's blue edge. Accordingly, the specific pixel characteristics at each point constrain the system, thereby providing accurate information about the three-dimensional location of the point. Other suitable 3D sensor assemblies include laser-scanning systems.

The illumination assembly (120) is configured to apply light in the visible spectrum to the specimen (150). The response of the specimen (150) to the applied light may be used to determine internal characteristics of the specimen (150) such as the spectroscopic information about the biochemical structure of a tissue specimen. An analysis of a tissue specimen is discussed in more detail below.

Exemplary Implementation and Operation

Figure 2:
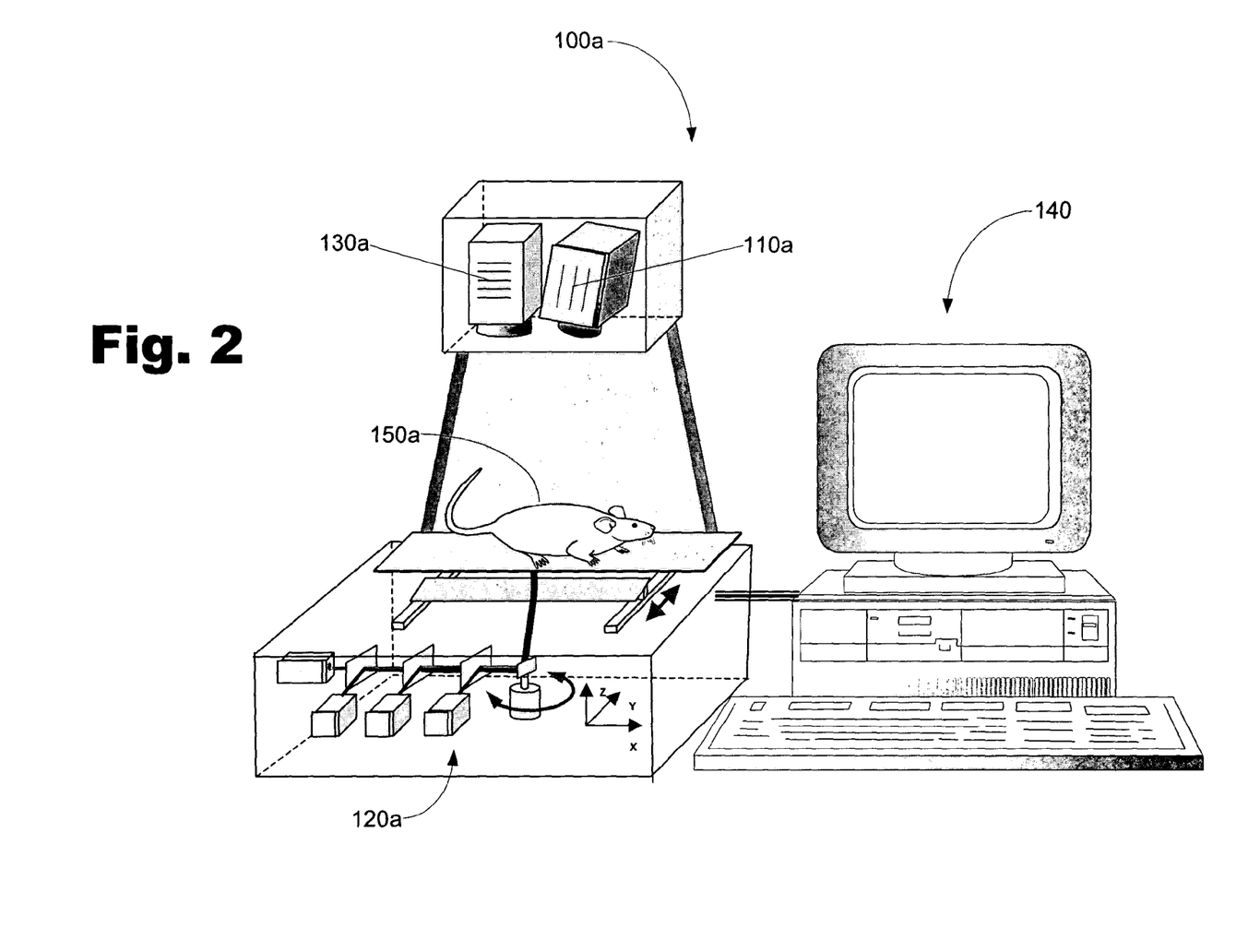
FIG. 2 illustrates a perspective view of an improved diffuse optical tomography system according to one exemplary embodiment.

FIG. 2 illustrates an improved diffuse optical tomography system (100a) similar to the implementation illustrated in FIG. 1, which is configured to characterize information about the biochemical structure and the three-dimensional boundary characteristics of a specimen (150a). The three-dimensional boundary characterization is accomplished by capturing and processing the specimen's (150a) response to the projection of a spatially varying wavelength spectrum by the spectrum source assembly (110a). The information about the biochemical structure, the tomographic data, is obtained by capturing and processing the specimen's response to illumination by the illumination assembly (120a). This spectroscopic information may reveal physiological parameters (e.g., oxygen saturation of hemoglobin and blood flow) based on intrinsic tissue contrast, molecular tissue function, as well as gene-expression based on extrinsically administered fluorescent probes and/or beacons.

Figure 3:
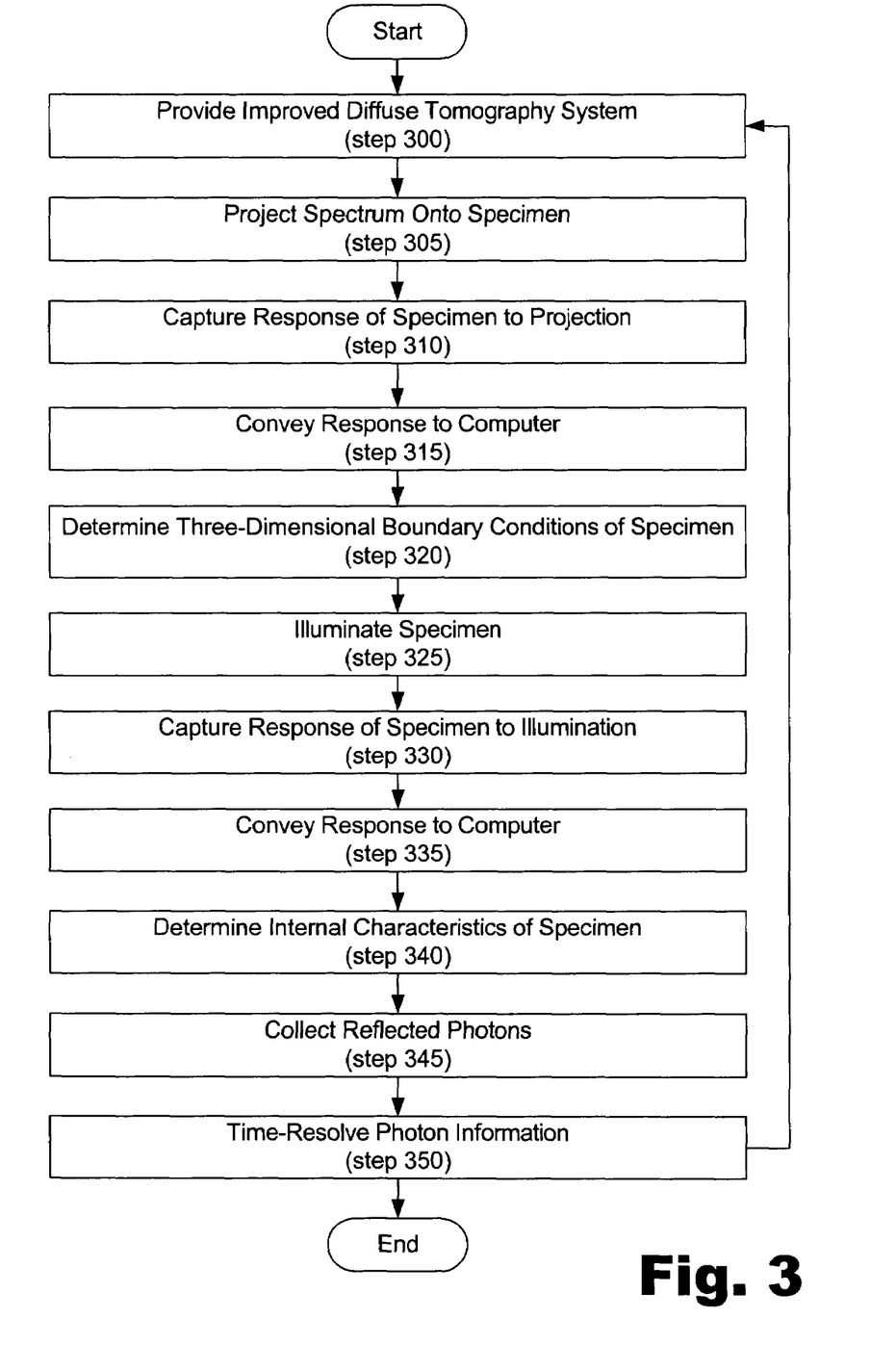
FIG. 3 is a flowchart illustrating a method of using an improved diffuse optical tomography system according to one exemplary embodiment.

FIG. 3 is a flowchart illustrating a method of using an improved diffuse optical tomography system. The method begins by providing an improved diffuse optical tomography system (step 300). The improved diffuse optical tomography system generally includes an illumination source assembly, a spectrum generating assembly, a sensor, and a computer. The computer directs the spectrum generating assembly to project at least one spectrum onto a specimen (step 305). The spectrum may be a spectrum of spatially varying wavelengths, such as that produced by an LVWF. The response of the specimen to the projected spectrum is then captured by the sensor (step 310) and conveyed to the computer (step 315). The computer processes the spectrum projection data in order determine the three-dimensional boundary conditions of the specimen (step 320). U.S. Pat. No. 5,675,407 to Geng issued Oct. 7, 1997 describes a novel three-dimensional surface profile measuring technique that is able to acquire full frame, dynamic 3-D images of objects with complex surface geometries at high speed. This patent is incorporated by reference in its entirety.

After acquiring and processing the three-dimensional boundary conditions (step 320), the computer directs the illumination source to illuminate a specimen (step 325). The response of the specimen to the illumination is captured by the sensor (step 330) and conveyed to the computer (335). The computer processes the illumination data in order to determine the internal characteristics of the specimen in the area of the illumination (step 340).

This processing may include processing calculation of a forward problem and an inverse problem. The forward problem is defined to predict the light propagation pattern traveling through scattering medium (such as human tissues), given the optical properties of the medium. The inverse problem is then set to estimate the tissue optical properties (reconstruct the images) based on the optical intensity distribution measured along the surface of the organ. Unlike the X-Ray photons that travel in virtually straight paths, optical photons traveling into tissue experience significant scattering form the cellular structures (mitochondria, other organelles and cellular membranes) and follow "diffuse" propagation patterns. Due to their diffuse pattern of propagation, NIR photons probe "volumes" and not "slices" as in other medical imaging techniques. Therefore tomographic techniques using real measurements of NIR photons reveal volumetric information and should be constructed as three-dimensional problems to better describe the underlying medium and improve accuracy. Efficient solutions to the forward problem exist by means of the diffusion approximation to the radiative transport or Boltzmann transport equation. The goal of DOT imaging is to reconstruct a spatial map of the optical contrast from fluence measurements at the boundary of the tissue of investigation. This is known as the "inverse problem". From these maps, other biological characteristics, such as maps of blood volume, oxygen concentration or gene-expression can be derived. The general idea for solving the inverse problem is to use an accurate forward problem that best predicts the photon propagation into the medium of investigation and compare its findings with the actual measurements in an iterative fashion that minimizes the difference between the fluence measurements and the forward model outputs.

Intrinsic tissue contrast may be captured that distinguishes between cancers and benign/normal lesions based on optical absorption and related to angiogenesis, apoptosis, necrosis, and hyper-metabolism; and optical scattering related to the size and concentration of cellular organelles. Extrinsic tissue contrast with the ability to resolve with high sensitivity gene-expression and molecular signatures in-vivo by resolving and quantifying novel classes of fluorochromes that probe specific molecular targets, such as cellular receptors, enzymes/proteins and nucleic acids.

DOT fundamentally produces quantitative images of intrinsic and extrinsic absorption, scattering and fluorescence as well as fluorochrome concentration and lifetime in diffuse media such as tissue. These fundamental quantities can then be used to derive tissue oxy- and deoxyhemoglobin concentrations, blood oxygen saturation, contrast agent uptake, fluorochrome activation and organelle concentration. Such novel contrast mechanisms are important for practical applications such as the measurement of tissue metabolic state, angiogenesis, and permeability for cancer detection, the measurement of functional activity in brain and muscle, the detection of hematomas and the elucidation of molecular pathways. Of particular importance are novel advances in fluorescent molecular probes and the ability to detect them in-vivo using fluorescence-mediated molecular tomography. The technology is a special application of DOT to molecular fluorescent probes and beacons and is explained in more detail due to the significant impact it may have into clinical research. The use of light in the visible spectrum is non-ionizing (photon energy is ~2 eV) that is substantially harmless in small doses. Accordingly, the use of light in the visible spectrum can be used for regular screening as well as continuous monitoring. Further, the use of visible light in the present system is non-invasive in that it does not require physical coupling between the light sources and the specimen. In addition, devices using visible light are relatively inexpensive and portable as compared to x-ray computed tomography (CT) and magnetic resonance imaging (MRI) and therefore could be used in emergency room applications, as well as for continuous bedside monitoring.

The accurate characterization of tissue spectral optical properties is important for accurate DOT inversions. The background optical properties may be measured on a per animal basis using time-resolved technology for the characterization of the average background absorption and reduces scattering coefficient. Light emanating 3–10 mm away from the impinging light source is collected through the mirror and lenses onto fiber bundles that are directed to a time-correlated diffuse spectrometer (reflectometer) (step 345). Multiple-distance measurements allow probing of tissues at different depths to allow for a more representative average value for tissue of the specimen examined. A photo-multiplier tube collects photons arriving after diffusing into tissue due to injected photon pulses with ~100 picosecond widths at very low powers. The detected photons generate electrical pulses at the output of the photon sensor that are subsequently time-resolved using a multi-channel analyzer unit (350). While photons propagating for source-sensor large separations could be detected by a standard photo-multiplier tube (PMT) for detection, here in it may be desirable to use a multi-channel-plate (MCP) due to the low separations proposed. A multi-channel plate allows for minimum photon-detection temporal blurring leading to small quantification errors. This is particularly important in this implementation due to the relative source-sensor proximity that yields relative short propagation times of photons in tissue. The detected data (called time resolved curves) are fitted to a Kirchoff Approximation solution of the diffusion equation for the forward problem using the geometry detected from the 3D imaging sensor, assuming flat surface for the central points that the animal resides on the positioning plate. Multiple detection points can be implemented using time-sharing of the fiber bundle outputs onto the same MCP-PMT sensor. Spectral information can be simultaneously acquired (up to 8 wavelengths) using appropriate time delays between the laser photon sources. Accordingly, the present method provides for rapid and near simultaneous acquisition of accurate three-dimensional boundary and tomographic data. This process may be repeated at as many points as necessary in order to obtain an appropriately detailed image.

Figure 4:
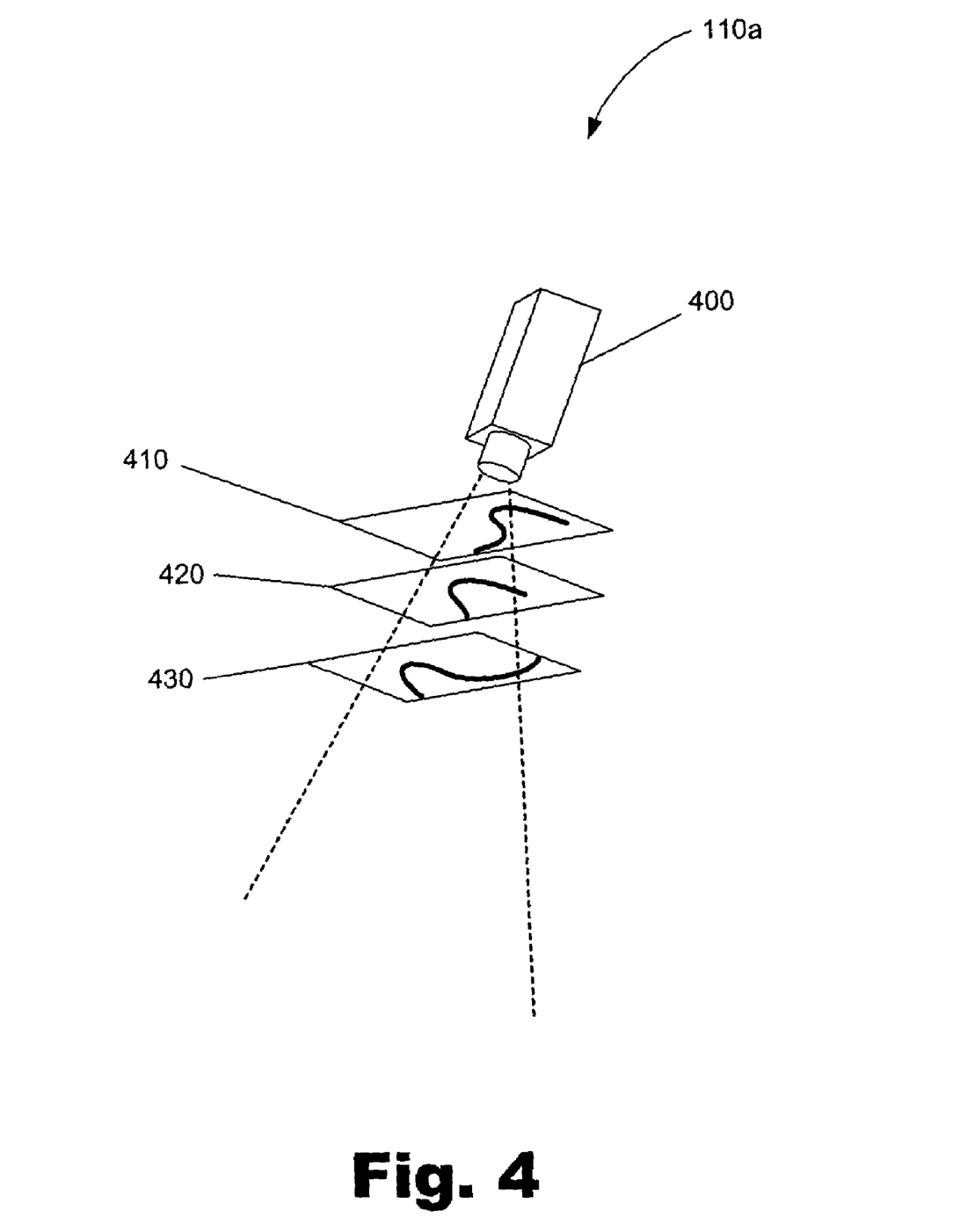
FIG. 4 illustrates a schematic view of a projection generation assembly used in one exemplary embodiment.
Figure 5:
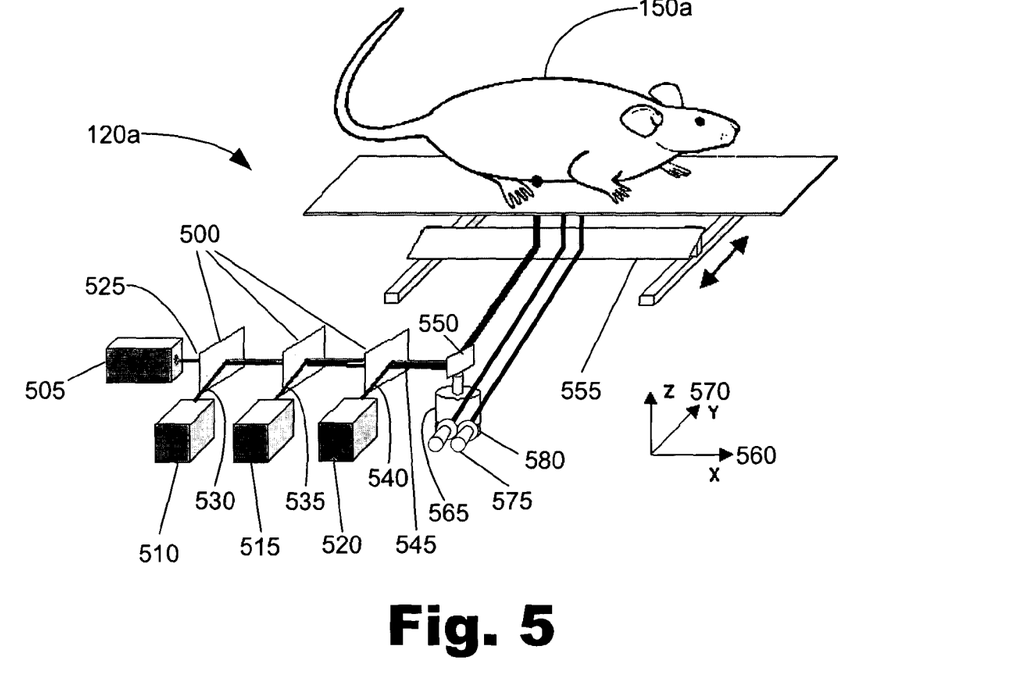
FIG. 5 illustrates a schematic view of an illumination assembly used in one exemplary embodiment.
Figure 6:
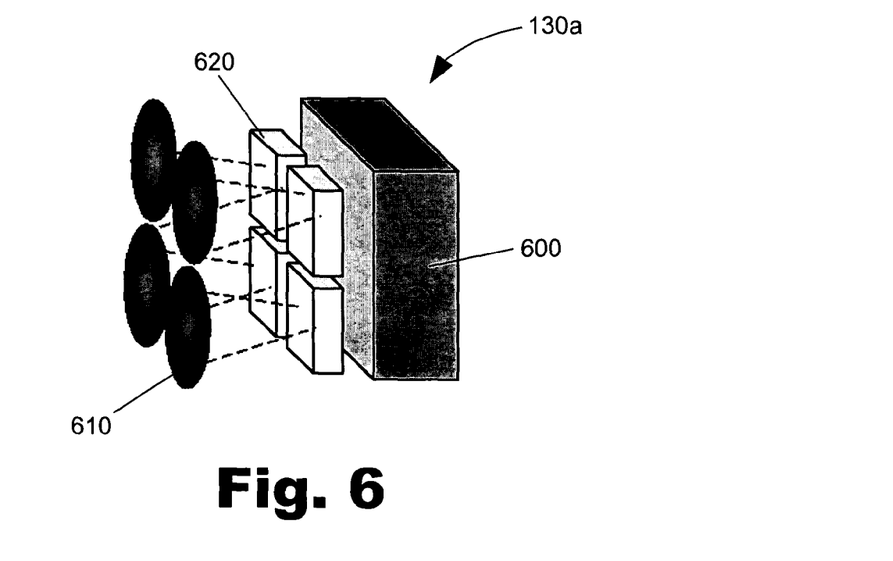
FIG. 6 illustrates a schematic view of a sensor used in one exemplary embodiment.

FIGS. 4–6 each illustrate components of the improved diffuse optical tomography system (100a) shown in FIG. 2 in more detail. FIG. 4 illustrates the spectrum source assembly (100a), FIG. 5 the illumination assembly (120a), and FIG. 6 the sensor assembly (130a) of FIG. 2.

FIG. 4 illustrates the spectrum source assembly (100a), which generally includes a projection light source (400) and filters (410, 420, 430). The projection light source (400) is a monochromic light projector. The filters (410, 420, 430) are three variable density filters whose density variation patterns are similar to the spectral characteristics of red green blue (RGB) filters of a CCD camera. In operation, the three filters (410, 420, 430) are sequentially placed in front of the projection light source (400) in order to form sequential light pattern projections. Monochromic image acquisitions are conducted to obtain one frame of image that is equivalent to that of a rainbow projection. Accordingly, the projection generating assembly is able to generate a spatially varying wavelength projection pattern, similar to that produced by an LVWF. Although three images are needed to form an equivalent rainbow projection pattern image, faster image acquisition is still possible by using high frame rate cameras. Further, the configuration of the spectrum source assembly (110a) minimizes or eliminates the need for the use of expensive color spectrum filters.

FIG. 5 illustrates the illumination assembly (120a) in more detail. The illumination assembly (120a) generates light within the spectral "window" for DOT imaging of soft tissue, which is between about 650 nm and 850 nm. As shown in FIG. 5, illumination assembly (120) includes beam-splitters (500) to combine light generated by laser sources (505, 510, 515, and 520) each of which produce beams of different wavelengths (525, 530, 535, and 540). These beams (525, 530, 535, and 540) are combined into a single composite beam (545) by the use of beam splitters (500). The beam splitters (500) are coated high-pass wavelength filters with transmission and reflectance properties selected to facilitate formation of the composite beam (545). The composite beam (545) is directed from the beam splitters (500) onto a location on the specimen (150a) by way of a rotary mirror (550) and a directional mirror (555).

The composite beam (545) may be directed to any location on the specimen (150a). Orientation of the composite beam (545) along the x-axis (560) is controlled by rotational motor (565), which is coupled to the rotazy mirror (550). The orientation of the composite beam (545) along the y-axis (570) is controlled by a linear motor (not shown) that is coupled to the directional mirror. Activation of both the rotational motor (565) and the linear motor (not shown) is controlled by computer (140; FIG. 2). This arrangement allows the light source configuration to be changed "on the fly" thereby facilitating the development of customized illumination plans for specific types of subjects, without changing the system hardware. Accordingly, the illumination assembly (120a) may be a multi-wavelength composite source that integrates multiple spectral light sources such as the lasers (505, 510, 515, and 520) into a single beam and positions the multi-spectral point-light spot onto any location on the surface of the specimen.

As previously discussed, background optical properties can be efficiently measured on a per animal basis using time-resolved methods. Light emanating from the illumination assembly (120a) is collected through lenses (575) onto fiber bundles (580) that are directed to a time-correlated diffuse spectrometer (reflectometer, not shown). Multiple-distance measurements will allow probing of tissues at different depths to allow for a more representative average value for tissue. The detected photons generate electrical pulses at the output of the photon sensor that are subsequently time-resolved using a multi-channel analyzer unit. While photons propagating for source-sensor large separations could be detected by a standard photo-multiplier tube (PMT) for detection, it may be necessary to use a multi-channel-plate (MCP) due to the low separations proposed. A multi-channel plate allows for minimum photon-detection temporal blurring leading to small quantification errors. This is particularly important in this implementation due to the relative source-sensor proximity that yields relatively short propagation times of photons in tissue. The detected data is fitted to the Kirchoff approximation solution of the diffusion equation for the forward problem using the geometry detected from the three dimensional imaging sensor, assuming flat surface for the central points that the animal resides on the positioning plate. Multiple detection points can be implemented using time-sharing of the fiber bundle outputs onto the same MCP-PMT sensor. Spectral information can be simultaneously acquired (up to 8 wavelengths) using appropriate time delays between the lasers (505, 510, 515, and 520).

The ability of DOT to image fluorochromes associated with molecular functions allows for three-dimensional imaging and quantifying of the up-regulation of cathepsin B in murine tumor models. Photon detection has high intrinsic sensitivity allowing the detection of fluorescent molecules at nano- to picomolar concentrations, similar to isotope concentrations in nuclear medicine. Fluorescent molecules may be quenched and de-quenched, enabling the design of molecular switches or "beacons". The probes are essentially non-fluorescent in their native (quenched) state and become highly fluorescent after enzyme-mediated release of fluorochromes, resulting in signal amplification of up to several hundred-fold, depending on the specific design. The use of multiple probes allows a single enzyme to cleave multiple fluorochromes, thus resulting in one form of signal amplification. Further, the reduction of background "noise" by several orders of magnitude is possible because very specific enzyme activities can potentially be interrogated while multiple probes can be arranged on delivery systems to simultaneously probe for a spectrum of enzymes.

Operation in intrinsic mode provides for characterization of internal processes as discussed above. Operation in fluorescence mode can direct the selection of wavelengths that are appropriate for excitation of the available dyes. The lasers (505, 510, 515, and 520) may be pulsed lasers with variable duty cycles. In pulsed mode, the lasers (505, 510, 515, and 520) may inject 100 mW of laser light onto the specimen for spectroscopic purposes. Alternatively, the lasers (505, 510, 515, and 520) may produce constant wattage beams of less than 50 mW. The lasers (The lasers (505, 510, 515, and 520) may be pulsed lasers with variable duty cycles. In pulsed mode, the lasers (505, 510, 515, and 520) may inject 100 mW of laser light onto the specimen for spectroscopic purposes. Alternatively, the lasers (505, 510, 515, and 520) may produce constant wattage beams of less than 50 mW. may be laser diodes as monochromic light sources because they are less expensive and easier to operate than other types lasers. Accordingly, the present system allows for selection between characterization of intrinsic or extrinsic characteristics as determined by constant or pulsed light conditions.

FIG. 6 illustrates an example in which the sensor (130; FIG. 1) is a multi-view multi-spectral camera (MMC) (130a) that generally includes a single CCD (charge-coupled device) sensor (600), lenses (610) and spectrum filters (620). The MMC (130a) is capable of simultaneously acquiring four images with different spectral bands. Each of the four quadrants of the sensor chip is covered by a spectrum filter (620) of a distinct wavelength. Since the camera uses one sensor chip that is split into four sub-areas, the temporal synchronization is simple—snapshot acquisition mode is used where all of the pixels are integrated over the same time period across the entire sensor (600). The spatial registration among multiple images is achieved by the precise design and alignment of the multiple aperture optical system. Since the MMC (130a) uses separate optical lenses (610) for the images in different spectral bands, precise alignment among the four quadrants becomes important. Each sensor has its awn optical image center and image parameters; there is no physical alignment among them that can be used for the inter-image alignment. Using a back projection scheme facilitates the precise alignment of all images in a pixel-by-pixel fashion, thus solving the very difficult inter-image alignment problem. Each of the four quadrants has approximately the same field of view (FOV) but there is no optical alignment among them. Therefore, the four images acquired by the sensor (600) cannot be simply overlaid together to offer pixel-level multi-spectral information. However, the three dimensional surface profile of the specimen is already acquired by recording and processing the specimen's (150) response to the spectrum projected by the spectrum source assembly (110a). Accordingly, accurate (x, y, z) geometric measurements of any visible surface point are available. Using these geometric measurements, it is possible to "back-project" the surface point onto the image sensor chip via a ray-tracing scheme, given tar the geometric parameters of each image sensor are know via a prior calibration procedures. The resulting coordinate values from each sensor will then be registered together as a multi-spectrum pixel set. Accordingly, the sensor (130a) is not only able to capture information about three-dimensional boundary conditions, but is also able to capture multi-spectral imaging information.

The information captured by the sensor (130a) is conveyed to and processed by the computer (140). In an intrinsic mode the four proposed wavelengths are used in pairs for characterization of oxy- and deoxy-hemoglobin. The intrinsic mode algorithm creates an over-determined system of two unknowns (oxy- and deoxy-hemoglobin) and four measurements, i.e. the absorption coefficients reconstructed at the four employed wavelengths. This approach significantly minimizes sensitivity to reconstruction noise. Alternatively, in a fluorescence mode the four wavelengths can be used to measure up to four different dyes selecting lasers at appropriate windows. The selection of dyes with excitation and emission responses at 50nm apart respectively suffice to minimize cross talk between simultaneous excitation of multiple dyes. The selection of appropriate wavelengths in this case will depend on laser availability and fluorescent dye/ molecular probe availability at the time of the implementation.

A single CCD sensor can be used to acquire both 2D intensity images and the images for 3D calculation. Since both 2D and 3D images are taken from a single sensor, any image registration issue is eliminated. There is no similar technology reported to date on this integrated 2D/3D sensing capability for DOT.

In fluorescence mode the four wavelengths can be used to measure up to four different dyes selecting lasers at appropriate windows. Typically, due to the close to monochromatic radiation, selections of dyes with excitation and emission responses at 50nm apart respectively suffice to minimize cross talk between simultaneous excitation of multiple dyes. The selection of appropriate wavelengths in this case will depend on laser availability and fluorescent dye molecular probe availability at the time of the implementation.

The computer (140; FIG. 2) controls the image acquisition process. Custom design software and graphic user interface will be developed to facilitate the ease of operation of acquiring multiple frames images of the same subject and are well known in the art.

ALTERNATIVE EMBODIMENTS

Figure 7:
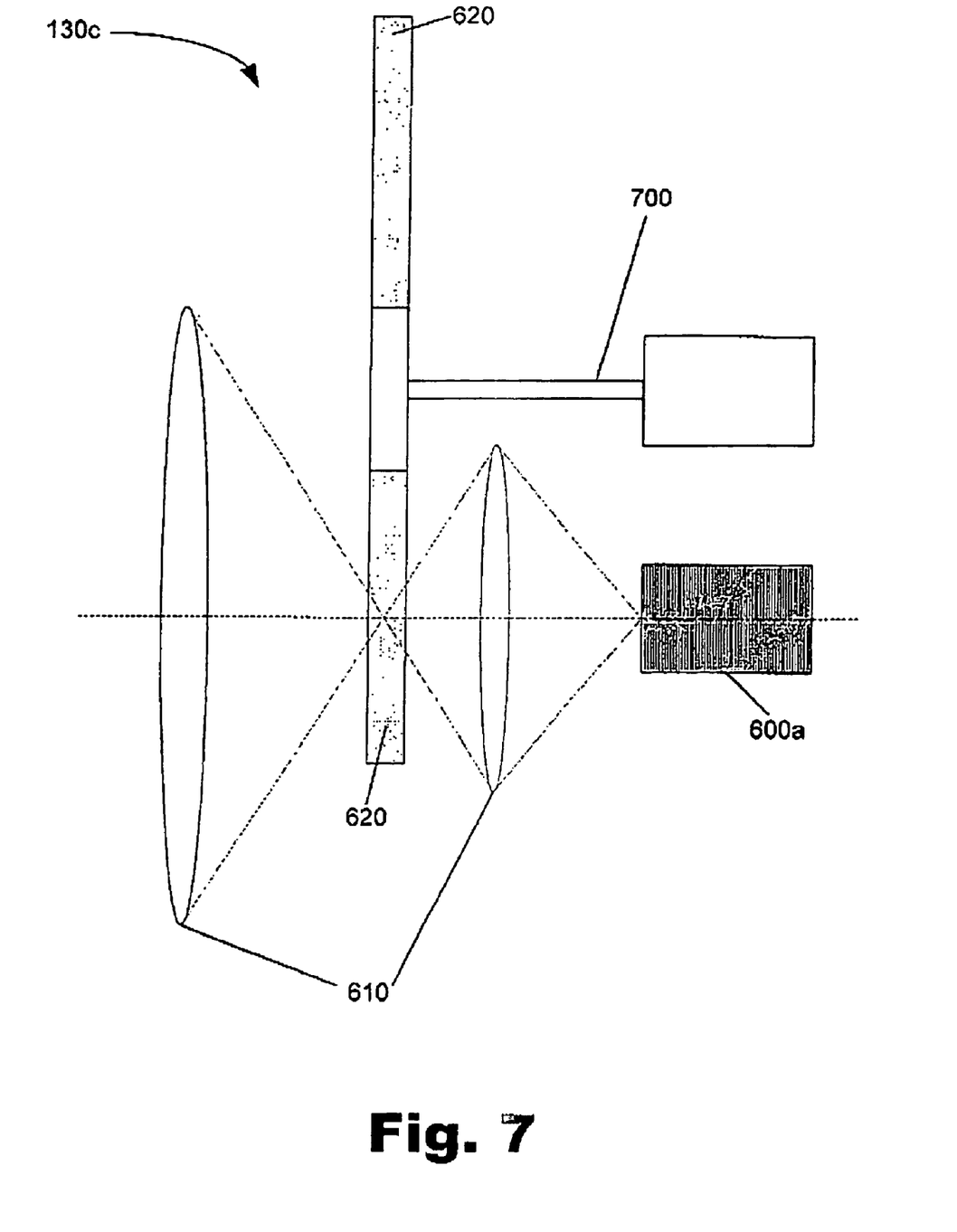
FIG. 7 illustrates a schematic view of a sensor used in one exemplary embodiment.

FIG. 7 illustrates a sensor assembly (130c) which includes a filter wheel (700) to which are attached a plurality of filters (620). Lenses (610) focus the incoming light onto the sensor (600a). The filter wheel (700) rotates in response to commands from the computer (140; FIG. 2) in order to place the proper filter (620) in the path of the light. Those of skill in the art will recognize that there are any number of configurations in which the individual elements of the composite beam (545; FIG. 5) may be separated.

In another embodiment, the spectrum source assembly (110; FIG. 1) includes a three-dimensional rainbow camera, in addition to the 2D sensor (130a, FIG. 2) described above. Any number of sensors and/or cameras may be utilized to capture the required data.

Further, in other embodiments, not shown, the spectrum source assembly is configured to project a plurality of LVWF's onto the specimen. Instead of changing the wavelength in single cycle, the projection pattern that varies the wavelength several times crossing the entire field of view. The multiple spectrum pattern illuminates the specimen (150; FIG. 1) with a greater wavelength variation rate to achieve higher sensitivity in color matching. The accuracy of the three-dimensional measurement may then be improved.

For each wavelength, there are multiple possible values of projection angles. There is no longer the one-to-one corresponding relationship in the MRP. Therefore, additional procedures are needed for the new 3D Camera to be able to distinguish the correct projection angle from multiple candidates resulting from the one-to-many table lookup. Although color-angle lookup table has a one-to-many mapping property with the use of multiple spectra, the search space may be restricted to a single cycle of rainbow variation to achieve a one-to-one correspondence. Within one cycle of the rainbow projection, the solution to color match is unique. When using a local search method in a one-to-many configuration, the outcome of the search relies heavily upon the initial condition. If a search starts within a neighborhood of the solution, it can achieve a correct result. If a search starts in a point far away from the solution, it may end up with a wrong answer. Accordingly, the initial point of a search is determined by a previously obtained correct match point adjacent to it.

While some of the preceding implementations utilize 'rainbow spectrum' projectors, any projection and sensor system capable of capturing three-dimensional boundary data may be used. Examples include, but are in no way limited to three-dimensional cameras or laser scanners. In addition, any illumination and sensor system capable of capturing DOT information may also be used. These systems may be combined and use a single structure or each of the systems may be used independently.

The preceding description has been presented only to illustrate and describe embodiments of invention. It is not intended to be exhaustive or to limit the invention to any precise form disclosed. Many modifications and variations are possible in light of the above teaching. It is intended that the scope of the invention be defined by the following claims.

What is claimed is:

1. An improved diffuse optical tomography system for in vivo non-contact imaging, comprising:
   an illumination source for illuminating a specimen;
   a spectrum source for projecting a spectrum onto said specimen; and
   at least one sensor configured to capture a response of said specimen to said illumination and said projection of said spectrum;
   wherein said illumination source comprises a plurality of lasers, wherein said plurality of lasers comprises four lasers, wherein said lasers are each configured to generate wavelengths between approximately 650nm and 800nm;
   further comprising a mirror assembly configured to project light from said lasers as a single beam onto said specimen.

2. The system of claim 1, wherein said mirror assembly comprises a plurality of motors configured to manipulate said mirror assembly to direct said single beam onto any desired point on said specimen.

3. An improved diffuse optical tomography system for in vivo non-contact imaging, comprising:
   an illumination source for illuminating a specimen;
   a spectrum source for projecting a spectrum onto said specimen;
   at least one sensor configured to capture a response of said specimen to said illumination and said projection of said spectrum; and a processor-based device configured to process data acquired by said sensor, said device producing and combining tomography data based on sensing of said illumination source and three-dimensional data of a surface of said specimen based on sensing of said spectrum source.

4. An improved diffuse optical tomography system for in vivo non-contact imaging, comprising:
   an illumination source for illuminating a specimen;
   a spectrum source for projecting a spectrum onto said specimen;
   at least one sensor configured to capture a response of said specimen to said illumination and said projection of said spectrum; and a processor-based device configured to control said illumination source, said spectrum source and a minor assembly for directing light from said illumination source onto said specimen.

5. An improved diffuse optical tomography system for in vivo non-contact imaging, comprising:
   an illumination source for illuminating a specimen;
   a spectrum source for projecting a spatially varying wavelength spectrum onto said specimen; and
   a sensor assembly configured to capture responses to said illumination and said projection of said spectrum;
   wherein said illumination source comprises four lasers, wherein said lasers are each configured to generate light between approximately 650nm and 800nm in wavelength; and
   further comprising a mirror assembly configured to project said light from said lasers as a single beam onto said specimen.

6. The system of claim 5, wherein said minor assembly comprises a plurality of motors configured to manipulate said minor assembly to direct said single beam onto a pre-determined location on said specimen.

7. An improved diffuse optical tomography system for in vivo non-contact imaging, comprising:
   an illumination source for illuminating a specimen;
   a spectrum source for projecting a spatially varying wavelength spectrum onto said specimen;
   a sensor assembly configured to capture responses to said illumination and said projection of said spectrum; and
   a processor-based device configured to control said illumination source and said spectrum source.

8. An improved DOT imaging system, comprising:
   means for capturing three-dimensional boundary characteristics of a surface of a specimen; and
   means for substantially simultaneously capturing DOT characteristics.

9. The system of claim 8, wherein said means for capturing three-dimensional boundary characteristics and said means for substantially simultaneous capturing DOT characteristics comprise independent sensor means.

10. The system of claim 8, wherein said means for capturing three-dimensional boundary characteristics and said means for substantially simultaneous capturing DOT characteristics comprise a shared sensor assembly.

11. The system of claim 8, further comprising means for processing said captured characteristics.

12. The system of claim 8, wherein said means for capturing three-dimensional boundary characteristics comprises a laser-scanner.

* * * * *

UNITED STATES PATENT AND TRADEMARK OFFICE
CERTIFICATE OF CORRECTION

| | | |
|---|---|---|
| PATENT NO. | : 7,107,116 B2 | Page 1 of 1 |
| APPLICATION NO. | : 10/654225 | |
| DATED | : September 12, 2006 | |
| INVENTOR(S) | : Z. Jason Geng | |

It is certified that error appears in the above-identified patent and that said Letters Patent is hereby corrected as shown below:

Column 11, Line 16, Claim 4, change "said spectrum source and a minor assembly" to --said spectrum source and a mirror assembly--

Column 11, Line 32 Claim 6, change "claim 5, wherein said minor assembly" to --claim 5, wherein said mirror assembly--

Column 12, Line 1, Claim 6 change "said minor assembly" to --said mirror assembly--

Signed and Sealed this

Fourteenth Day of November, 2006

JON W. DUDAS
*Director of the United States Patent and Trademark Office*